United States Patent [19]

Sensui et al.

[11] Patent Number: 4,749,796

[45] Date of Patent: Jun. 7, 1988

[54] XANTHENE DERIVATIVE AND A PRODUCTION PROCESS OF THE SAME

[75] Inventors: Hideyuki Sensui, Tokyo; Michihiro Gonda, Kitamoto; Toshio Obara, Kawaguchi, all of Japan

[73] Assignee: Hodogaya Chemical Co., Ltd., Tokyo, Japan

[21] Appl. No.: 805,699

[22] Filed: Dec. 6, 1985

[30] Foreign Application Priority Data

Dec. 7, 1984 [JP] Japan .................. 59-257431

[51] Int. Cl.$^4$ .......................... C07D 311/82
[52] U.S. Cl. .................... 549/225; 549/226; 549/227
[58] Field of Search ............ 549/225, 226, 227

[56] References Cited

U.S. PATENT DOCUMENTS

| | | | |
|---|---|---|---|
| 2,946,750 | 7/1960 | Odell et al. ............ | 252/49.7 X |
| 3,658,543 | 4/1972 | Gerlach, Jr. et al. ....... | 96/90 |
| 4,067,840 | 1/1978 | Wolf ..................... | 523/210 |
| 4,306,014 | 12/1981 | Kunikane et al. ......... | 430/156 |
| 4,370,401 | 1/1983 | Winslow et al. ........... | 430/171 X |

FOREIGN PATENT DOCUMENTS

| | | |
|---|---|---|
| 0005380 | 11/1979 | European Pat. Off. . |
| 44002 | 6/1888 | Fed. Rep. of Germany . |
| 6054381 | 3/1985 | Japan . |

OTHER PUBLICATIONS

Nishikawa, Chemical Abstracts, vol. 90 (1979), 130,635e.
Kunikane et al., Chemical Abstracts, vol. 94 (1981), 74714y.
Pikaev et al., Chemical Abstracts, vol. 95 (1981), 117041s.
Matsushita Elect., Chemical Abstracts, vol. 95 (1981), 178617f.
Chemical Abstracts, 102 (1985), 123125b.
Chemical Abstracts, 102 (1985), 70290t.

*Primary Examiner*—Richard L. Raymond
*Attorney, Agent, or Firm*—Sherman and Shalloway

[57] ABSTRACT

This invention relates to a xanthene derivative that develops color on oxidation, so that it is favorably used for a photoresist, a PS plate or a proofing agent. The xanthene derivative, which has the following structural formula (I), is produced by putting a fluoran derivative represented by the following structural formula (II) to an esterification reaction and then to a reduction reaction.

In the above formulae $R_1$ and $R_2$ independently stand for hydrogen, an alkyl radical with 1 to 8 carbon atoms, a tetrahydrofurfuryl radical, a substitued or an unsubstituted phenyl radical, a substituted or an unsubstituted benzyl radical or a cyclic alkyl radical; in addition, $R_1$ and $R_2$ are able to form a ring in pairs. $R_3$ and $R_6$ independently stand for hydrogen, chlorine, fluorine, a lower alkyl radical or a lower alkoxy radical. $R_4$ and $R_5$ independently stand for hydrogen, chlorine, fluorine, a lower alkyl radical, a lower alkoxy radical, a lower alkoxyalkyl radical, a substituted or an unsubstituted phenyl radical, a substituted or an unsubstituted benzyl radical, an amino radical, a N-substituted or N,N-substituted amino radical or a cyclic alkyl radical; in addition, $R_3$ and $R_4$, $R_4$ and $R_5$, and $R_5$ and $R_6$ are able to form a ring in pairs respectively. $R_7$ stands for an alkyl radical, a substituted or an unsubstituted phenyl radical or a substituted or an unsubstituted benzyl radical. X stands for hydrogen, chlorine, fluorine, bromine, a nitro radical, a lower alkyl radical or a lower alkylamino radical; and n stands for an integer from 1 to 4 inclusive.

12 Claims, No Drawings

XANTHENE DERIVATIVE AND A PRODUCTION PROCESS OF THE SAME

FIELD OF THE INVENTION

This invention relates to a xanthene derivative. More particularly, this invention relates to a novel xanthene derivative which is useful as a precursor of colorants mainly employed for a photoresist, a PS plate, a proofing agent and the like, a production process of the same and a composite for giving an image, which includes the same.

DESCRIPTION OF THE PRIOR ART

A composite which forms an image developing colour on irradiation is very important for preventing double exposures in manufacturing a PS plate or a photoresist or confirming the positioning of a photomask; besides it is used as a simple proofing agent (See Japanese Patent Publication Laid-Open Nos. sho 55-13780 and sho 59-142545.). Among many such composites, an organic polyhalogen compound and a combination of a photooxidizing agent and various leuco dyes (See Japanese Patent Publication Laid-Open Nos. sho 59-140447, sho 59-142545 and sho 47-12879.) are typical. However, the former is toxic and the latter, which contains leucotriphenylmethane as a leuco dye, not only has a problem in stability but is imperfect in colour performance as none of the combinations turns black.

SUMMARY OF THE INVENTION

Accordingly, the present inventors have studied intensively to eliminate the above drawbacks and found that a novel xanthene derivative represented by the structural formula (I) makes a stable, colorless solid product in the air and turns red, orange, green, blue or black on oxidation so favorably as to be used for a photoresist, a PS plate and a proofing agent; thus, they have accomplished this invention. That is to say, this invention consists of:

(1) a xanthene derivative represented by the structural formula (I) which develops colour on oxidation

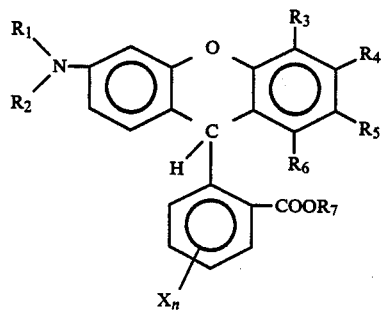

(I)

(In the above formula, $R_1$ and $R_2$ independently stand for hydrogen, an alkyl radical with 1 to 8 carbon atoms, a tetrahydrofurfuryl radical, a substituted or an unsubstituted phenyl radical, a substituted or an unsubstituted benzyl radical or a cyclic alkyl radical; in addition, $R_1$ and $R_2$ are able to form a ring in pairs; $R_3$ and $R_6$ independently stand for hydrogen, chlorine, fluorine, a lower alkyl radical or a lower alkoxy radical; $R_4$ and $R_5$ independently stand for hydrogen, chlorine, fluorine, a lower alkyl radical, a lower alkoxy radical, a lower alkoxyalkyl radical, a substituted or an unsubstituted phenyl radical, a substituted or an unsubstituted benzyl radical, an amino radical, a N-substituted or N,N-substituted amino radical or a cyclic alkyl radical; in addition, $R_3$ and $R_4$, $R_4$ and $R_5$, and $R_5$ and $R_6$ are able to form a ring in pairs respectively; $R_7$ stands for an alkyl radical, a substituted or an unsubstituted phenyl radical or a substituted or an unsubstituted benzyl radical; X stands for hydrogen, chlorine, fluorine, bromine, a nitro radical, a lower alkyl radical or a lower alkylamino radical; and n stands for an integer from 1 to 4 inclusive.), (2) a production process of a xanthene derivative represented by the structural formula (I), which is characterized by putting a fluoran derivative represented by the structural formula (II) to an esterification reaction and then to a reduction reaction

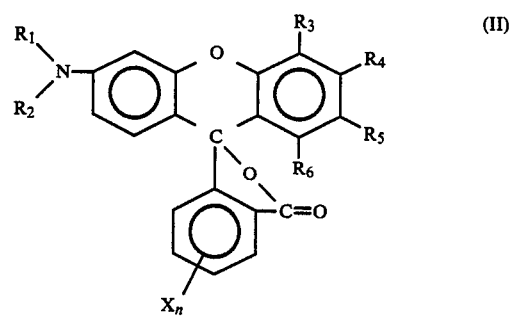

(II)

(In the above formula, $R_1$, $R_2$, $R_3$, $R_4$, $R_5$, $R_6$, X and n stand for the same as those in the above.), and (3) a composite for giving an image, which includes a xanthene derivative represented by the structural formula (I).

DETAILED DESCRIPTION OF THE INVENTION

Referring now closely to every radical in the structural formula (I), which represents a novel xanthene derivative of this invention, $R_1$ and $R_2$ independently stand for methyl radical, ethyl radical, propyl radical, butyl radical, pentyl radical, isopentyl radical, hexyl radical, heptyl radical, octyl radical, tetrahydrofurfuryl radical, phenyl radical, o-, m-, or p-tolyl radical, xylyl radical, benzyl radical or cyclohexyl radical.

$R_3$ and $R_6$ independently stand for chlorine, fluorine, methyl radical, ethyl radical, propyl radical, butyl radical, methoxy radical, ethoxy radical, propoxy radical or butoxy radical.

$R_4$ and $R_5$ stand for chlorine, fluorine, methyl radical, ethyl radical, butyl radical, pentyl radical, isopentyl radical, hexyl radical, heptyl radical, octyl radical, methoxy radical, ethoxy radical, propoxy radical, butoxy radical, ethoxyethyl radical, ethoxymethyl radical, methoxyethyl radical, phenyl radical, o-, m-, or p-tolyl radical, xylyl radical, benzyl radical, o-, m-, or p-chlorobenzyl radical, amino radical, methylamino radical, ethylamino radical, propylamino radical, butylamino radical, phenylamino radical, o-, m-, or p-chlorophenylamino radical, tetrahydrofurfurylamino radical, benzylamino radical, o-, m-, or p-chlorobenzylamino radical, dimethylamino radical, diethylamino radical, dipropylamino radical, dibutylamino radical, diphenylamino radical, di(o-, m-, or p-chlorophenyl)-amino radical, ditetrahydrofurfurylamino radical, dibenzylamino radical or di(o-, m-, or p-chlorophenyl) amino radical.

$R_7$ stands for methyl radical, ethyl radical, propyl radical, butyl radical, phenyl radical, o-, m-, or p-chlorophenyl radical, benzyl radical or o-, m-, or p-chlorobenzyl radical.

X stands for chlorine, fluorine, bromine, nitro radical, methyl radical, ethyl radical, propyl radical, diethylamino radical, dimethylamino radical or butyl radical.

A novel xanthene derivative represented by the structural formula (I) can be given by putting a fluoran derivative represented by the structural formula (II) to an esterification reaction and then to a reduction reaction. Although examples of the fluoran derivative are disclosed in Japanese Patent Publication Laid-Open No. sho 55-13780, for instance, other fluoran derivatives, such as 2-(2-chlorophenyl)-amino-6-N,N-dibutylaminofluoran, 2-N,N-dibenzylamino-6-N,N-diethylamino fluoran, Rhodamine F-3B, etc. can also be used in this invention. These fluoran derivatives are put to reaction in order to open their lactone ring and invert a substituent at 9th position into an ester radical. The reaction is accomplished by causing the fluoran derivatives to react with an alcohol or a phenol derivative in the presence of an acid.

More specifically, such acids as sulfuric acid, hydrochloric acid and toluenesulfonic acid, etc., commonly used in an esterification reaction, will do; nonetheless, hydrochloric acid is desirable in the case. Also, methyl alcohol, ethyl alcohol, benzyl alcohol, phenol and the like are used in the capacity of the alcohol or the phenol derivative mentioned above.

In this invention, another esterification is also possible; namely, it is accomplished by causing the fluoran derivatives to react with an alkyl halide or dialkyl sulfate at 20°-100° C. for 1-10 hours in general.

A product resulting from the esterification reaction is next put to a reduction reaction; thereby, in a case, sodium borohydride is used as a reducing agent; in the other, platinum oxide, palladium carbon or Raney nickel are used in the catalytic reaction as a reducing agent.

A xanthene derivative thus produced is a colorless or slightly colored solid stable in the air, as aforementioned. The solid product turns red, orange, green, blue or black upon oxidation. Therefore, a composite for giving an image can be prepared by making use of this property. For this reason, the term "composite", as the term is employed herein, is meant by a composite that contains a xanthene derivative represented by the structural formula (I), which is used for giving an image. And the composite denotes a material which is used to prevent double exposure or confirm the positioning of a photomask in manufacturing a proofing agent, a PS plate, a photoresist and the like.

Meantime, the composite is composed of: (1) a photo oxidizing agent, (2) a xanthene derivative represented by the structural formula (I), (3) a colour development auxiliary agent and (4) a binder, provided a fixing agent may be added according to requirements.

A photo oxidizing agent is inactive in a usual condition, but when it is put under radiation of visible, ultraviolet or X ray, it forms a chemical substance capable of causing a leuco dye to develop colour on oxidation. Among this kind of photo oxidizing agents are hexaarylbiimidazole as disclosed in Japanese Patent Publication No. sho 43-19161, a pyridinium compound as disclosed in the U.S. Pat. No. 3,615,568, an azido compound as disclosed in the U.S. Pat. No. 3,282,693 and an aromatic iodide as disclosed in the U.S. Pat. No. 4,368,154, for example.

Referring now to these products, 2,2'-bis(2-chlorophenyl)-4,5,4',5'-tetraphenyl-1,2'-biimidazole, 2,2'-bis(2-chlorophenyl) 4,5,4',5'-tetrakis(3-methoxyphenyl)-1,2'-biimidazole, 2,2'-bis(2-chloro-4-methoxyphenyl)-4,5,4',5'-tetraphenyl-1,2'-biimidazole, 2,2'-bis(2,4-dichlorophenyl)-4,5,4',5'-tetraphenyl-1,2'-biimidazole, 2,2'-bis(2-nitrophenyl)-4,5,4',5'-tetraphenyl-1,2'-bimiidazole, 2-azidobenzoxazole, benzoylazide, 2-azidobenziimidazole, 3-ethyl-1-methoxy-2-pyridothiacyanine perchlorate, 1-methoxy-2-methylpyridinium-p-toluenesulfonate, diphenyliodonium nitrate, diphenyliodonium hexafluorophosphate, etc. can be employed in the capacity of the photo oxidizing agent mentioned above.

Furthermore, as a concrete example of the xanthene derivative of this invention, 2-(2-chlorophenyl)-amino-6-N,N-dibutyl-amino-9-(2-methoxycarbonyl)-phenylxanthene, 2-N,N-dibenzylamino-6-N,N-diethylamino-9-(2-methoxycarbonyl)-phenylxanthene, N,N,N',N'-tetraethyl-3,6-diamino-9-(2-ethoxycarbonyl)phenylxanthene, benzo[a]-6-N,N-diethylamino-9-(2-methoxycarbonyl)-phenylxanthene, 2-(2-chlorophenyl)-amino-6-N,N-diethylamino-9-(2-methoxycarbonyl)-phenylxanthene, 2-anilino-3-methyl-6-N-methyl-N-cyclohexylamino-9-(2-methoxycarbonyl)-phenylxanthene, etc. can be cited. In addition to these compounds, an additive salt composed of the xanthene derivatives and inorganic acids like hydrochloric acid, sulfuric acid, nitric acid and the like, or an organic acid like oxalic acid, p-toluenesulfonic acid, benzenesulfonic acid and the like can also be cited as a concrete example.

As a colour development auxiliary agent of this invention, mineral acids or aromatic sulfonic acids as disclosed in Japanese Patent Publication Laid-Open No. sho 59-140447, and polyethers can be put to the use. Specifically, hydrogen chloride, hydrogen bromide, sulfuric acid, benzenesulfonic acid, nitric acid, phosphoric acid, p-toluenesulfonic acid, benzenesulfonic acid, p-chlorobenzenesulfonic acid, 1-naphthalenesulfonic acid, 2-naphthalenesulfonic acid can be exemplified.

A resin which can be used favorably as a binder in this invention includes polystyrene, polyvinyl butyral, polyvinyl chloride, polymethylmethacrylate, polycarbonate, vinyl chloridevinyl acetate copolymer, styrenebutadiene copolymer, acetyl cellulose and so on.

When the composite of this invention is used for a photoresist, it may contain a photo-hardening agent. Specifically, hydroxyethylmethacrylate, diethyleneglycoldiacrylate, N,N'-methylenebisacrylamide, trimethylolpropanetriacrylate, pentaerithritol triacrylate and the like are used as the photohardening agent mentioned above.

Other than the above components, a fixing agent can also be added when fixing is required. That is, a redox coupler, a guanidine derivative, an alkylenediamine as disclosed in Japanese Patent Publication No. sho 43-19161 and Japanese Patent Publication Laid-Open No. sho 59-140447 can be used for the aim. Specifically, a combination of polyethylene glycol and 1,6-pyrenequinone, 1,3-diphenylguanidine, triphenylguanidine, hexamethylenediamine, etc. can be put to practical use.

A variety of papers, baryta papers, synthetic papers and films can be employed as a carrier for the composite of this invention. An organic solvent which can be employed favorably in applying the composite to the carrier includes toluene, benzene, xylene, tetrahydrofuran, acetone, methylethylketone, cyclohexane, acrylonitrile, methanol, ethanol, methylcellosolve, ethylcellosolve, ethylacetate, dioxane and the like.

When this invention is actually put into practice, the composite is desired to be concocted in the following proportion.

| *Xanthene derivative | 1.0 part |
|---|---|
| *Photo-oxidizing agent | 0.1–10 " |
| *Colour development auxiliary agent | |
| acid | 0.1–2.0 " |
| polyether | 0.5–10 " |
| *Binder | 1.0–50 " |
| *Photo-hardening agent | 0.1–50 " |
| *Fixing agent | 0.1–50 " |

This invention will be understood more readily with reference to the following examples; however, these examples are intended to illustrate the invention and not to be construed to limit the scope of this invention.

EXAMPLE 1

Preparation of 2-(2-chlorophenyl)-amino-6-N,N-dibutylamino-9-(2-methoxycarbonyl)-phenylxanthene

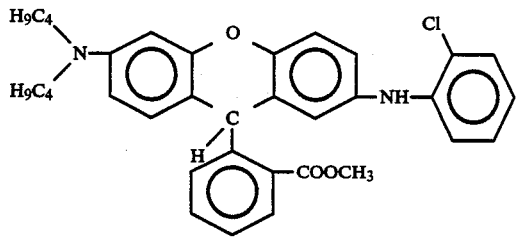

Thirty gr. of 2-(2-chlorophenyl)-amino-6-N,N-dibutylaminofluoran was dissolved in 250 ml of methanol. The fluoran derivative was put to an esterification reaction at 60° C. for 6 hours while hydrogen chloride gas was being introduced into the reaction system through a pipe. A resulting product was put in 1 l of water to give precipitation. The precipitate was filtered and dried; as a result, 13.9 gr. of an esterified product was obtained. The esterified product was dissolved in 900 ml of methanol. A reaction was carried out for 3 hours while 2.75 gr. of sodium borohydride was being added a little by a little.

A resulting solution was poured into 2 l of water. Extraction of a product was made by the use of 200 ml of toluene, which was removed later by steam distillation. There appeared a crude crystal, which was recrystallized in a solution mixture of ethanol and toluene. The recrystallization gave 10.7 gr. of 2-(2-chlorophenyl)-amino-6-N,N-dibutylamino-9-(2-methoxycarbonyl)-phenylxanthene, which showed a melting point 106°–110° C. The xanthene derivative turned black upon chloranil oxidation in a 95% acetic acid solution; $\lambda_{max}$ was present at 440 and 585 nm. The xanthene derivative was recognized to have the empirical formula $C_{35}H_{37}N_2O_3Cl$ by the following analytical result.

| | C | H | N |
|---|---|---|---|
| Theoretical value | 73.86 | 6.55 | 4.92 |
| Experimental value | 74.02 | 6.61 | 4.90 |

A $C^{13}$-NMR analysis also identified the recrystallized product as 2-(2-chlorophenyl)-amino-6-N,N-dibutylamino-9-(2-methoxycarbonyl)-phenylxanthene.

EXAMPLE 2

Preparation of 2-N,N-dibenzylamino-6-N,N-diethylamino-9-(2-methoxycarbonyl)-phenylxanthene

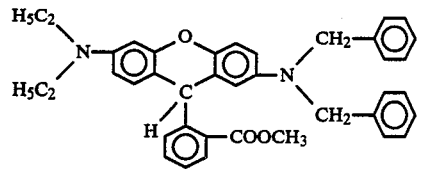

Thirty gr. of 2-N,N-dibenzylamino-6-N,N-diethylaminofluoran was dissolved in 250 ml of methanol. The fluoran derivative was put to reaction at 60° C. for 6 hours while hydrogen chloride gas was being introduced into the reaction system through a pipe. A resulting product was put in 1 l of water to give precipitation. The precipitate was filtered and dried. A cake thus provided was dissolved in 900 ml of methanol and kept standing in reaction for 2 hours while 7 gr. of sodium borohydride was being added a little by a little. A resulting solution was poured into 2 l of water. Extraction of a product was made by the use of 200 ml of toluene, which was evaporated later to give a crude crystal.

As a result of recrystallizing the crude crystal in ethyl acetate, 13.1 gr. of 2-N,N-dibenzylamino-6-N,N-diethylamino-9-(2-methoxycarbonyl)-phenylxanthene appeared. The compound melted at 113°–115° C. and turned green upon chloranil oxidation in a 95% acetic acid solution; $\lambda_{max}$ was present at 444, 448 and 600 nm. The compound was recognized to have the empirical formula $C_{39}H_{38}N_2O_3$ by the following analytical result.

| | C | H | N |
|---|---|---|---|
| Theoretical value | 80.38 | 6.57 | 4.81 |
| Experimental value | 80.62 | 6.50 | 4.92 |

EXAMPLE 3

Preparation of N,N,N',N'-tetraethyl-3,6 diamino-9-(2-ethoxycarbonyl)-phenylxanthene

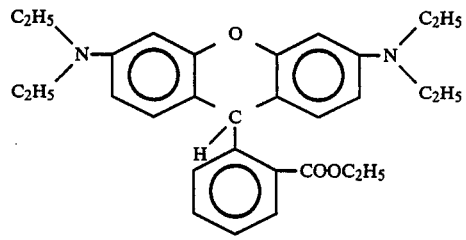

At first, 32.4 gr. of Rhodamine F-3B was dissolved in 650 ml of ethanol. It was put to reaction at 30°–40° C.

for 5 hours while sodium borohydride was being added gradually. After the reaction, a resulting product was put in 1.5 l of water and a crystal thus precipitated was filtered. As a result of recrystallizing the crystal in a toluene-ethanol mixture solution, 17.8 gr. of N,N,N',N'-tetraethyl-3,6-diamino-9-(2-ethoxycarbonyl)phenylxanthene was produced. The compound melted at 129°–130° C. and turned red upon chloranil oxidation in methanol; $\lambda_{max}$ was present at 554 nm. The compound was recognized to have the empirical formula $C_{30}H_{36}N_2O_3$ by the following analytical result.

|  | C | H | N |
|---|---|---|---|
| Theoretical value | 76.24 | 7.68 | 5.93 |
| Experimental value | 76.04 | 7.65 | 5.90 |

EXAMPLE 4

Preparation of benzo[a]-6-N,N-diethylamino-9-(2-methoxycarbonyl)-phenylxanthene

Thirty gr. of benzo[a]-6-N,N-diethylamino-fluoran was dissolved in 250 ml of methanol. The fluoran derivative was put to reaction at 60° C. for 6 hours while hydrogen chloride gas was being introduced into the reaction system by way of a pipe. The resulting solution was put in 1 l of water to give precipitation. The precipitate was filtered; there appeared 28 gr. of an esterified product, which was then dissolved in 700 ml of methanol and put to a catalytic reaction at room temperatures under normal pressure for 6 hours by using 0.2 gr. of platinum oxide. After filtered, the resulting solution was put in 2 l of water to give precipitation. After filtered, the precipitate was recrystallized in toluene; thus, 21.0 gr. of benzo[a]-6-N,N-diethylamino-9-(2-methoxycarbonyl)phenylxanthene was obtained. The compound was slightly yellow and showed a melting point 159°–160° C. Moreover, it turned red on chloranil oxidation in a 95% acetic acid solution; $\lambda_{max}$ was present at 523 and 557 nm. The following analytical result reveals that it has the empirical formula $C_{29}H_{27}NO_3$.

|  | C | H | N |
|---|---|---|---|
| Theoretical value | 79.61 | 6.22 | 3.20 |
| Experimental value | 79.41 | 6.31 | 3.24 |

EXAMPLES 5 to 28

A variety of new xanthene derivatives produced similarly to the above are shown in the following Table 1.

TABLE 1

| Ex. | R₁ | R₂ | R₃ | R₄ | R₅ | R₆ | R₇ | X | n | λ_max (nm) |
|---|---|---|---|---|---|---|---|---|---|---|
| 5 | —C₂H₅ | —C₂H₅ | H | H | 2-Cl-C₆H₄-NH— | H | —CH₃ | H | 4 | 436, 580 |
| 6 | —CH₃ | cyclohexyl | H | CH₃ | C₆H₅-NH— | H | —CH₃ | H | 4 | 450, 593 |
| 7 | —C₂H₅ | —CH₂—CH₂—CH(CH₃)—CH₃ | H | CH₃ | C₆H₅-NH— | H | —C₂H₅ | H | 4 | 449, 596 |
| 8 | —CH₂-(2,2-dimethyl-1,3-dioxolane) | —C₂H₅ | H | CH₃ | C₆H₅-NH— | H | —CH₃ | H | 4 | 452, 594 |
| 9 | —C₄H₉ | —C₄H₉ | H | CH₃ | C₆H₅-NH— | H | —CH₃ | H | 4 | 450, 590 |
| 10 | —C₂H₅ | —C₂H₅ | H | CH₃ | H | CH₃ | —C₂H₅ | H | 4 | 496, 528 |
| 11 | —C₂H₅ | —C₂H₅ | H | H | 2-Cl-C₆H₄-NH— | H | —CH₃ | —CH₃ | 1 | 438, 583 |

TABLE 1-continued

| Ex. | $R_1$ | $R_2$ | $R_3$ | $R_4$ | $R_5$ | $R_6$ | $R_7$ | X | n | $\lambda_{max}$ (nm) |
|---|---|---|---|---|---|---|---|---|---|---|
| 12 | $-C_2H_5$ | $-C_2H_5$ | H | H | $-CH_2-N(C_6H_5)(CH_2-o-ClC_6H_4)$ | H | $-CH_3$ | H | 4 | 434, 606 |
| 13 | $-C_2H_5$ | $-C_2H_5$ | $-OCH_3$ | H | $-NH-C_6H_5$ | H | $-CH_3$ | H | 4 | 446, 470, 612 |
| 14 | $-C_2H_5$ | $-C_2H_5$ | H | $-C_6H_5$ | $-NH-C_6H_5$ | H | $-C_2H_5$ | H | 4 | 451, 605 |
| 15 | $-C_2H_5$ | $-C_2H_5$ | H | H | $-NH-C_6H_4$-$p$-COCH$_3$ | H | $-C_6H_5$ | H | 4 | 440, 583 |
| 16 | $-CH_3$ | cyclohexyl | H | $-CH_3$ | $-NH-C_6H_5$ | H | $-CH_3$ | $-CH_3$ | 1 | 453, 594 |
| 17 | $-C_2H_5$ | $-C_2H_5$ | H | $-N(C_2H_5)_2$ | H | H | $-CH_3$ | H | 4 | 554 |
| 18 | $-C_2H_5$ | H | H | $-NH(C_2H_5)$ | H | H | $-C_2H_5$ | H | 4 | 550 |

TABLE 1-continued
| Ex. | $R_1$ | $R_2$ | $R_3$ | $R_4$ | $R_5$ | $R_6$ | $R_7$ | X | n | $\lambda_{max}$ (nm) |
|---|---|---|---|---|---|---|---|---|---|---|
| 19 | H | H | H | —N(CH$_3$)$_2$ | H | H | —C$_2$H$_5$ | H | 4 | 552 |
| 20 | —CH$_3$ |  | H | —CH$_3$ | H | H | —CH$_2$— | H | 4 | 452, 590 |
| 21 |  |  | H | —N(C$_6$H$_5$)$_2$ | H | H | —CH$_3$ | H | 4 | 575 |
| 22 |  |  | H | —N(p-tolyl)$_2$ | H | H | —C$_2$H$_5$ | H | 4 | 583 |
| 23 |  |  | H | —N(m-tolyl)$_2$ | H | H | —CH$_3$ | H | 4 | 578 |

TABLE 1-continued

| Ex. | R₁ | R₂ | R₃ | R₄ | R₅ | R₆ | R₇ | X | n | λ$_{max}$ (nm) |
|---|---|---|---|---|---|---|---|---|---|---|
| 24 | —C₂H₅ | —C₂H₅ | H | —N(C₆H₅)₂ | H | H | —CH₃ | H | 4 | 568 |
| 25 | —CH₃ | —C₆H₅ | H | —N(CH₃)(C₆H₅) | H | H | —CH₃ | H | 4 | 545 |
| 26 | —C₆H₅ | —C₆H₅ | H | —N(4-CH₃-C₆H₄)₂ | H | H | —CH₃ | H | 4 | 574 |
| 27 | —C₆H₅ | —(4-OCH₃-C₆H₄) | H | —N(C₆H₅)(4-OCH₃-C₆H₄) | H | H | —CH₃ | H | 4 | 585 |
| 28 | —C₆H₅ | —(4-Cl-C₆H₄) | H | —N(C₆H₅)(4-Cl-C₆H₄) | H | H | —CH₃ | H | 4 | 578 |

λ$_{max}$: on chloranil oxidation in a 95% acetic acid solution

Examples that the xanthene derivatives of this invention are used as a proofing agent will be outlined as follows.

APPLICATION EXAMPLE 1

Two composites I and II were prepared separately as shown below. The composite II was applied to a sheet of paper at a rate of 40 gr./m² with a 0.5 m/m bar coater and then dried; the composite I was applied thereon at a rate of 30 gr./m² and dried. A photographic negative film was laid on top of a sensitive paper thus produced. The sensitive paper developed into a black image after 5 minutes' exposure on a vacuum printing frame (P-113-B type product manufactured by Dai Nihon Screen Co., Ltd.). A subsequent 5-minute-heat-treatment at 100° C. gave a permanent image that never causes discoloration upon re-exposure.

| Composite I (for colour development) | |
|---|---|
| *2-(2-chlorophenyl)-amino-6-N,N—dibutylamino-9-(2-methoxycarbonyl)-phenylxanthene | 0.4 part |
| *2,2'-bis(2-chlorophenyl)-4,5,4',5'-tetraphenyl-1,2'-biimidazole | 0.35 " |
| *p-toluenesulfonic acid monohydrate | 0.41 " |
| *polyethyleneglycol | 1.04 " |
| *vinyl chloride-vinyl acetate copolymer | 2.00 " |
| *tetrahydrofuran | 20.00 " |
| *ethanol | 4.00 " |

| Composite II (for fixing) | |
|---|---|
| *1,3-diphenyl guanidine | 0.41 " |
| *polyvinyl alcohol | 1.00 " |
| *70% ethanol | 20.00 " |

For a comparative application example, another composite for colour development was prepared in the same way as the composite I, except that the above xanthene derivative was replaced by leucocrystal violet. The procedure and treatment to develop an image were also the same as the above; as a result, there appeared a blue image. Table 2 shows the difference between the two cases.

TABLE 2

| | Colour | Image density | Fog density |
|---|---|---|---|
| Example | Black | 1.1 | 0.16 |
| Comparative Example | Blue | 1.4 | 0.32 |

A Macbeth RD-514 reflection densitometer was employed in the measurement of image density and fog density. Leucocrystal violet gave a fog as dense as 0.32, whereas the xanthene derivative gave one a half as dense as that; the latter turned black by itself on oxidation.

APPLICATION EXAMPLES 2, 3, 4 and 5

In place of the xanthene derivative used in Application Example 1, xanthene derivatives prepared in Examples 2, 3, 4 and 5 were used to give a permanent image, wherein the procedure and treatment were left unchanged. The following table shows their result. The result of leucoethyl violet is shown for a comparative example.

TABLE 3

| Xanthene derivative of | Colour | Image density | Fog density |
|---|---|---|---|
| Example 2 | green | 1.3 | 0.17 |
| Example 3 | red | 1.8 | 0.20 |
| Example 4 | red | 1.2 | 0.12 |
| Example 5 | black | 1.1 | 0.14 |
| Leucoethyl violet | blue | 1.3 | 0.42 |

It becomes clear that the xanthene derivatives generally give an image much more free from fog than leucoethyl violet does.

What is claimed is:

1. A xanthene derivative represented by the structural formula (I)

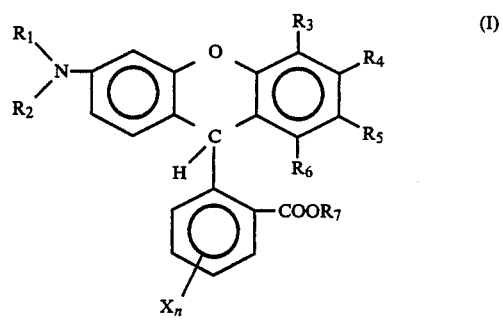

which is colorless or only slightly colored, is stable in air and develops colour on oxidation wherein $R_1$ and $R_2$ independently stand for hydrogen, an alkyl radical with 1 to 8 carbon atoms, a tetrahydrofurfuryl radical, a phenyl radical, a benzyl radical or a cyclic alkyl radical; in addition, $R_1$ and $R_2$ are able to form a ring in pairs; $R_3$ and $R_6$ independently stand for hydrogen, chlorine, fluorine, a lower alkyl radical or a lower alkoxy radical; $R_4$ stands for hydrogen, chlorine, fluorine, a lower alkyl radical, a lower alkoxy radical, a lower alkoxyalkyl radical, a phenyl radical, a benzyl radical or a cyclic alkyl radical; $R_5$ stands for hydrogen, chlorine, fluorine, a lower alkyl radical, a lower alkoxy radical, a lower alkoxyalkyl radical, a phenyl radical, a benzyl radical, an amino radical, or a cyclic alkyl radical; $R_7$ stands for an alkyl radical, a phenyl radical or a benzyl radical, when any one of $R_1$, $R_2$, $R_4$, $R_5$ or $R_7$ is a phenyl radical or a benzyl radical the phenyl radical and benzene radical may be unsubstituted or may be substituted by chlorine, fluorine, lower alkyl radical or lower alkoxy radical and when $R_5$ is an amino radical the amino radical may be unsubstituted or may be N-substituted or N,N-disubstituted with a substituent selected from the group consisting of a lower alkyl radical, unsubstituted phenyl radical, a phenyl radical substituted with chlorine, fluorine, a lower alkyl radical, a lower alkoxy radical or an acetyl radical, an unsubstituted benzyl radical and a benzyl radical substituted with chlorine, fluorine, a lower alkyl radical or a lower alkoxy radical; in addition, $R_3$ and $R_4$, $R_4$ and $R_5$, and $R_5$ and $R_6$ are able to form a ring in pairs respectively, X stands for hydrogen, chlorine, fluorine, bromine, a nitro radical, a lower alkyl radical or a lower alkylamino radical; and n stands for an integer from 1 to 4 inclusive.

2. The xanthene derivative of the structural formula (I) according to claim 1 wherein
$R_1$ and $R_2$, independently, represent hydrogen, methyl, ethyl, propyl, butyl, pentyl, isopentyl, hexyl, heptyl, octyl, tetrahydrofurfuryl, phenyl, o-, m-, or p-tolyl, xylyl, benzyl or cyclohexyl;

R³ and R⁶, independently, represent hydrogen, chlorine, fluorine, methyl, ethyl, propyl, butyl, methoxy, ethoxy, propoxy or butoxy;

R₄ represents hydrogen, chlorine, fluorine, methyl, ethyl, butyl, pentyl, isopentyl, hexyl, heptyl, octyl, methoxy, ethoxy, propoxy, butoxy, ethoxyethyl, ethoxymethyl, methoxyethyl, phenyl, o-, m-, or p-tolyl, xylyl, or benzyl; R₅ represents hydrogen, chlorine, fluorine, methyl, ethyl, butyl, pentyl, isopentyl, hexyl, heptyl, octyl, methoxy, ethoxy, propoxy, butoxy, ethoxyethyl, ethoxymethyl, methoxyethyl, phenyl, o-, m-, or p-tolyl, xylyl, or benzyl, o-, m-, or p-chlorobenzyl, amino, methylamino, ethylamino, propylamino, butylamino, phenylamino, o-, m-, or p-chlorophenylamino, tetrahydrofurfurylamino, benzyl-amino, o-, m-, or p-chlorobenzylamino, dimethylamino, diethylamino, dipropylamino, dibutylamino, diphenylamino di(o-, m-, or p-chlorophenyl)-amino, ditetrahydrofurfurylamino, dibenzylamino or di(o-, m-, or p-chlorophenyl)amino;

R₇ represents methyl, ethyl, propyl, butyl, phenyl, o-, m-, or p-chlorophenyl, benzyl, or o-, m-, or p-chlorobenzyl; and X represents hydrogen, chlorine, fluorine, bromine, nitro, methyl, ethyl, propyl, butyl, diethylamino, or dimethylamino.

3. The xanthene derivative represented by the structural formula (I) as set forth in claim 1 which is 2-(2-chlorophenyl)-amino-6-N,N-dibutyl-amino-9-(2-methoxycarbonyl)-phenylxanthene.

4. The xanthene derivative represented by the structural formula (I) as set forth in claim 1 which is 2-N,N-dibenzylamino-6-N,N-diethylamino-9-(2-methoxycarbonyl)-phenylxanthene.

5. The xanthene derivative represented by the structural formula (I) as set forth in claim 1 which is benzo-6-N,N-diethylamino-9-(2-methoxycarbonyl)-phenylxanthene.

6. The xanthene derivative represented by the structural formula (I) as set forth in claim 1 which is 2-(2-chlorophenyl)-amino-6-N,N-diethylamino-9-(2-methoxycarbonyl)phenylxanthene.

7. The xanthene derivative represented by the structural formula (I) set forth in claim 1 which is 2-anilino-3-methyl-6-N-methyl-N-cyclohexylamino-9-(2-methoxycarbonyl)-phenylxanthene.

8. A production process of a xanthene derivative represented by the structural formula (I) as set forth in claim 1, which is characterized by subjecting a fluoran derivative represented by the structural formula (II)

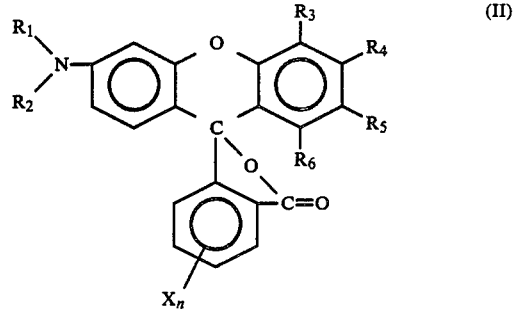

wherein R₁–R₆, X and n are as defined, to an esterification reaction and then to a reduction reaction.

9. A production process of a xanthene derivative according to claim 8 in which said esterification reaction is made between said fluoran derivative and an alcohol or a phenol derivative in the presence of an acid.

10. A production process of a xanthene derivative according to claim 8 in which said esterification reaction is made between said fluoran derivative and an alkyl halide or a dialkyl sulfate.

11. A production process of a xanthene derivative according to claim 8 in which sodium borohydride is used in said reduction reaction as a reducing agent.

12. A production process of a xanthene derivative according to claim 8 in which platinum oxide, palladium on carbon, or Raney nickel is used in said reduction reaction as a reducing agent.

* * * * *